United States Patent [19]

Brown et al.

[11] Patent Number: 5,786,215

[45] Date of Patent: Jul. 28, 1998

[54] METHOD FOR CULTURING ANIMAL CELLS

[75] Inventors: Peter C. Brown, Menlo Park; Mark T. Wininger, Benicia; Robert V. Oakley, Lafayette, all of Calif.

[73] Assignee: Baxter International Inc., Deerfield, Ill.

[21] Appl. No.: 436,648

[22] Filed: May 8, 1995

Related U.S. Application Data

[62] Division of Ser. No. 299,322, Aug. 31, 1994, abandoned, which is a continuation of Ser. No. 971,672, Nov. 4, 1992, abandoned, which is a continuation of Ser. No. 635,422, Jan. 3, 1991, abandoned, which is a continuation of Ser. No. 52,682, May 20, 1987, abandoned.

[51] Int. Cl.$^6$ ............... C12N 5/00; C12M 3/06
[52] U.S. Cl. ......... 435/401; 435/399; 435/297.2
[58] Field of Search ............... 435/240.23, 240.2, 435/240.241, 240.242, 297.2, 297.4, 395, 398, 399, 400, 401, 402; 422/48; 210/321.72, 321.75, 321.76, 321.8, 321.84, 321.85, 321.89

[56] References Cited

U.S. PATENT DOCUMENTS

| | | | |
|---|---|---|---|
| 3,489,647 | 1/1970 | Kolobow | 435/2 |
| 3,792,978 | 2/1974 | Freedman | 422/48 |
| 3,892,533 | 7/1975 | Freedman | 23/258.5 |
| 3,948,732 | 4/1976 | Haddad | 195/127 |
| 4,128,479 | 12/1978 | Malchesky et al. | 422/48 |

FOREIGN PATENT DOCUMENTS

| | | | |
|---|---|---|---|
| 2178447 | 2/1987 | United Kingdom | 435/285 |

*Primary Examiner*—William H. Beisner
*Attorney, Agent, or Firm*—St. Onge Steward Johnston & Reens LLC

[57] ABSTRACT

An apparatus and method for the in vitro culturing of animal cells, e.g., mammalian cells, to attain mass growth of the cells per se and/or to recover cell-secreted products of interest therefrom, in which an integral culture and gassing element is formed from spirally-wound or concentrically-wrapped lengths of a liquid-impermeable, oxygen-permeable membrane envelope such that narrow cell culture spaces are formed between adjacent windings or wrapping of the envelope. Cells in the culture spaces, which spaces may optionally contain cell substrate material, are cultured in contact with a culture medium introduced into the spaces from an end of the element, and in contact with oxygen-containing gas supplied to the membrane envelope for diffusion across its oxygen-permeable walls into the culture spaces.

5 Claims, 3 Drawing Sheets

METHOD FOR CULTURING ANIMAL CELLS

This is a divisional of application Ser. No. 08/299,322, filed on Aug. 31, 1994, now abandoned, which is a continuation of Ser. No. 07/971,672, filed Nov. 4, 1992, now abandoned, which is a continuation of Ser. No. 07/635,422, filed Jan. 3, 1991, now abandoned, which is a continuation of Ser. No. 07/052,682, filed May 20, 1987, now abandoned.

BACKGROUND OF THE INVENTION

The present invention relates to the in vitro culturing of animal cells and, more particularly, to methods and apparatus useful for the in vitro culturing of animal cells either for purposes of obtaining mass quantities of the cells per se or for purposes of recovering secreted products of interest from the cells.

For many years the art has been familiar with the in vitro culturing of animal cells for purposes, e.g., of studying cell-cell interactions, studying or assaying interactions between cells and various exogenous substances or fluids, and other like purposes. Among the most important motivations for the in vitro culturing of animal cells, however, particularly of late, are its utilization for the production of mass quantities of the cells and its utilization for recovery of useful products produced and secreted by the culturing cells.

The prior art is replete with methods and apparatus for the in vitro culturing of animal cells for purposes of growing up the cells to substantial density per se and/or for obtaining quantities of useful products (e.g., proteins) secreted by them. Anchorage-dependent cells, i.e., those which require affixation to a substrate surface in order to grow and survive, have been grown in a variety of flasks and roller bottles (where attachment is to the flask or bottle surfaces), on microcarriers suspended in culture medium, on the surfaces of hollow fibers, and in other like systems, while cells capable of surviving unattached to a substrate have been grown in a variety of suspension culture vessels, hollow fiber devices, and the like. Some of these techniques have achieved varying degrees of success, while others have not. Agreement uniformly exists in the art that improvement is needed in the in vitro culturing of mammalian cells.

SUMMARY OF THE INVENTION

It is an object of the present invention to provide a method and apparatus for the in vitro culture of animal cells.

A further object of the invention is to provide a method and apparatus for the continuous in vitro culture of animal cells.

Yet another object of the present invention is to provide a method and apparatus for the in vitro culture of animal cells and the collection therefrom of secreted cellular products of interest.

These and other objects are achieved in accordance with the present invention by provision of an animal cell culturing method and apparatus in which an integral culture and gassing element is provided, comprised of a plurality of generally concentric, generally annular, lengths of a liquid-impermeable, oxygen-permeable membrane envelope. The concentric, narrow, annular areas (generally arranged to be less than about one millimeter) between adjacent lengths of the oxygen-permeable membrane envelope define cell culture spaces in which cells to be cultured are maintained and bathed in culture medium introduced from one end face of the culture and gassing element, and from which culture fluid (i.e., spent culture medium containing in certain cases secreted cell products) can be withdrawn from the other end face. Oxygen-containing gas is provided to the interior of the membrane envelope and diffuses into the culture spaces across at least one oxygen-permeable layer forming the membrane envelope. The culture and gassing element is enclosed within a fluid-tight housing having means for providing culture medium, means for withdrawing culture fluid, accesses to gas inlet and gas outlet ports formed as part of the membrane envelope, and means for introducing cells into the culture spaces.

In the preferred embodiment of the invention the integral culture and gassing element is comprised of at least one length of a liquid-impermeable, oxygen-permeable membrane envelope, having gas inlet and outlet ports, which is spirally wound or rolled about itself (preferably beginning with a first wind about a supporting core material) so as to form the plurality of generally concentric, generally annular, substantially equal lengths of membrane envelope in which spaces between adjacent winds define generally concentric, generally annular, narrow cell culture spaces along the length of the element. By reason of the spiral configuration, these culture spaces are in fluid communication.

The liquid-impermeable, oxygen-permeable membrane envelope employed in the present invention comprises a sealed composite of two liquid-impermeable layers sandwiched about an inert spacer element. At least one, but preferably both, of the liquid-impermeable layers is oxygen-permeable such that oxygen-containing gas introduced into the envelope interior can diffuse across the layer into the culture spaces. According to one embodiment of the present invention, cells are cultured in contact with the outer surface of at least one of the liquid-impermeable layers forming the membrane envelope. In a more preferred embodiment, however, at least a portion of the length of at least some of the culture spaces between the adjacent membrane envelope winds (or lengths) are provided with a separate cell substrate upon which the cells anchor (or in association with which the cells are substantially immobilized in the culture spaces). This substrate can be, for example, a compound or composition (e.g., collagen) which can be applied to outer surfaces of at least one of the layers forming the membrane envelope. Alternatively, and preferably, the substrate can be one or more integral elements, such as sheets of appropriate substrate material or a plurality of fibers which, in turn, optionally can be provided with compounds or substances promoting cell adhesion. In yet another embodiment of the invention, inert spacer elements (i.e., other than cell substrate) can be arranged in the cell culture spaces as might be desirable to insure that these spaces are sized so as to easily accommodate cell growth, liquid flow and gas diffusion.

The method and apparatus of the present invention primarily address a significant problem plaguing known animal cell culture methods, to wit, the difficulty of providing sufficient oxygenation to the culturing cells so as to permit them to grow and/or produce product and/or secrete product, in the presence of nutrient medium, substantially as they do or would do in a natural in vivo environment. Many attempts have been made in the past to achieve this goal. For example, many culturing methods gassify the nutrient medium itself, but it is found that the oxygencarrying capacity of nutrient medium generally is too low to provide an effective means for oxygenating many types of animal cells, particular in culture units in which the medium must traverse along anything more than minimal length since most of the oxygen carried by the medium is lost early on in the traverse. Suggestions for utilization of separate oxygen-carrying particles or substances have been made but do not appear to have attained any degree of success. The same is true with respect to suggestions for culture units having separate gassing circuits, whether for direct contact with the cells or contact therewith across a gas-permeable membrane. In all cases, problems with elaborate unit design, trade-offs between efficient gas exchange and efficient contact with nutrient medium, and other like problems limit the usefulness of such proposed methods.

Central to the present invention is the utilization of a gas-providing means which efficiently delivers oxygen-containing gas along the full area of the culture unit, in close proximity to the culturing cells, in a manner which does not interfere with cell attachment or immobilization or with nutrient feed or culture fluid removal. Indeed, as will be seen, the present invention makes use of what is essentially a recognized, highly efficient oxygenator for blood, or artificial lung, and the surprising finding that such a device can be utilized, with certain modifications, as a cell culture unit per se.

Further details regarding the invention are explained with reference to the figures and detailed description which follows.

DETAILED DESCRIPTION OF THE INVENTION

Figure 1:
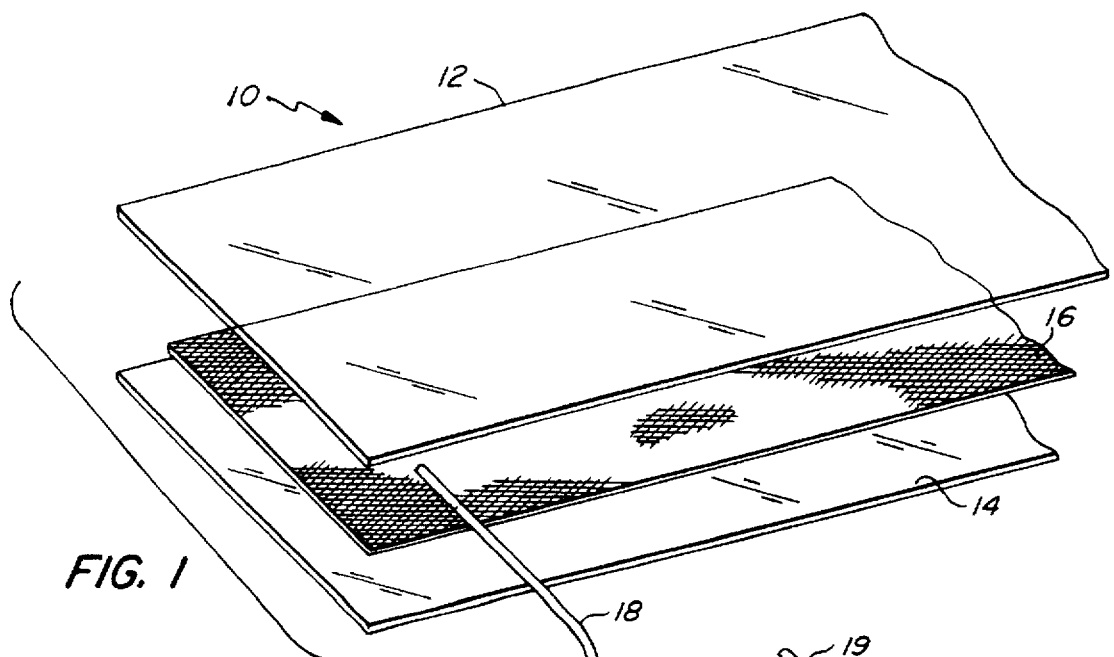
FIG. 1 is a perspective view illustrating the components of an oxygen-permeable membrane envelope for use in the present invention.
Figure 2:
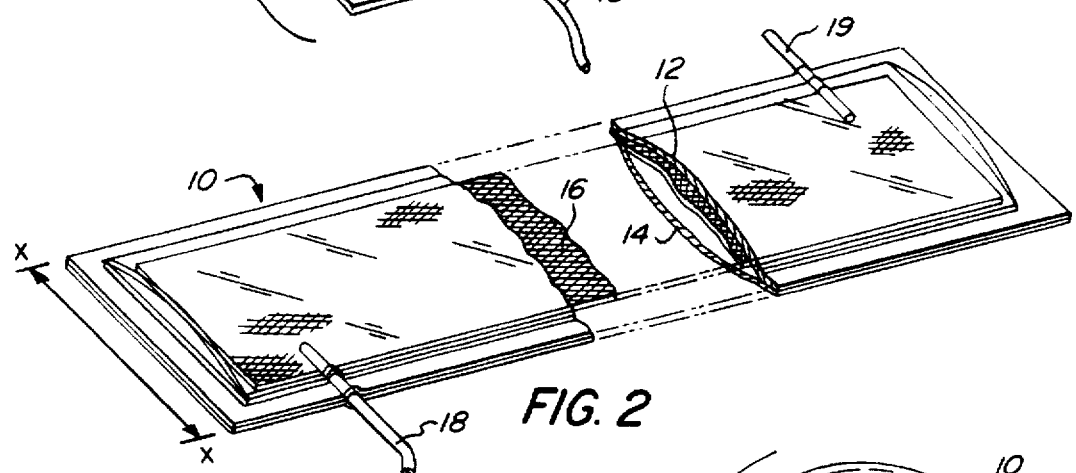
FIG. 2 is a perspective view illustrating the oxygen-permeable membrane envelope in its sealed condition.

According to the invention, and as illustrated in FIGS. 1 and 2, the liquid-impermeable, oxygen-permeable membrane envelope 10 is comprised of spacer element 16 interleaved between a top layer 12 and bottom or base layer 14. Top layer 12 and base layer 14 are formed of liquid-impermeable material and at least one of the layers also is oxygen-permeable. In the preferred embodiment of the invention, both top and base layers are oxygen-permeable. Suitable liquid-impermeable, oxygen-permeable materials for these layers are the known silicone rubbers, or materials such as polyethylene, polypropylene or polytetrafluoroethylene. Spacer element 16, employed to prevent collapse of the membrane envelope, can be formed of any suitable inert material, such as polypropylene, fiberglass, Saran, nylon or other polymeric plastics, typically in a porous screen or mesh-like configuration. A gas inlet port 18 and a gas outlet port 19, constructed, for example, of silicone rubber tubing, are arranged along lengths of the sealed composite envelope. Depending upon the length of the envelope, more than one set of inlet and outlet ports can be provided. The composite of spacer 16 and top and base layers 12 and 14 is sealed about its edges in any appropriate manner to provide an enclosed space within the envelope for introduction of oxygen-containing gas which can exit only by diffusion across an oxygen-permeable layer or through a gas outlet port.

As noted, the sealed oxygen-permeable membrane envelope can be utilized per se as the integral culture and gassing element of the invention by winding or rolling the envelope about itself, preferably making the first wind about a centrally-disposed supporting core element having a length substantially the same as the transverse dimension (dimension X—X in FIG. 2) of the envelope. In such form, the spirally-wound envelope is, in essential respects, a known and available blood oxygenator variously referred to in the art as a coil-type membrane oxygenator or a Kolobow unit. See, e.g., Nosé, "Manual On Artificial Organs", Vol. II, "The Oxygenator", pp. 157–159 (1973). See also, U.S. Pat. Nos. 3,489,647 and 3,892,533 and Canadian Patent No. 1,023,631, all of which are incorporated by reference herein, and which show further details of construction of envelope assemblies for coil or spool-type oxygenators. In this form, the cell culture areas defined by adjacent lengths of winds of the envelope are bounded solely by the outer surfaces of the liquid-impermeable, oxygen-permeable layers (e.g., layers 12 and 14) of the envelope. For certain animal cells, these surfaces constitute adequate substrate surfaces upon which the cells can affix and grow (or in association with which the cells can be substantially immobilized in the culture spaces and grow), or can be made to be suitable by appropriate smoothing or roughening of such surfaces, but this may not be possible, or optimum, for other animal cells.

Accordingly, in the preferred embodiment of the invention, the culture spaces of the integral culture and gassing element are provided with a separate independent cell substrate material.

Figure 3:
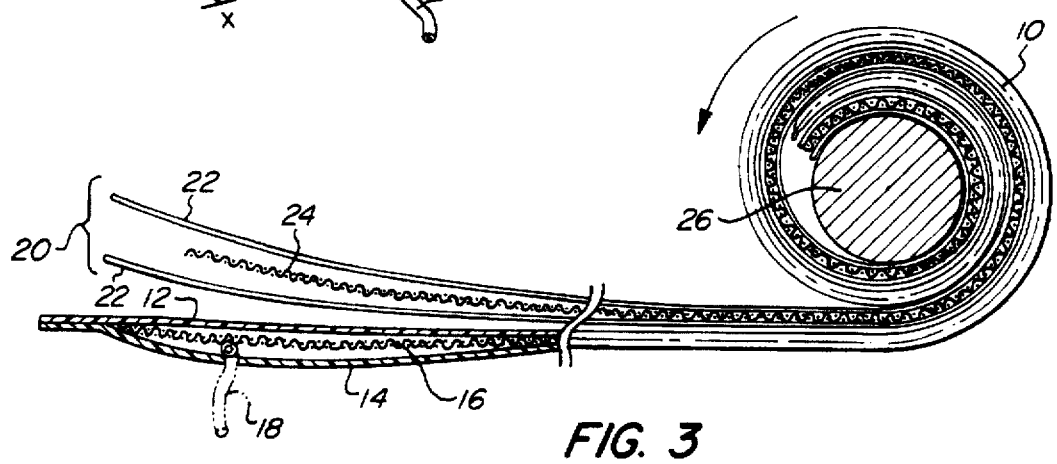
FIG. 3 is an end view, diagrammatic representation of the components of, and method for assembling, an integral culture and gassing element according to the invention.
Figure 6:
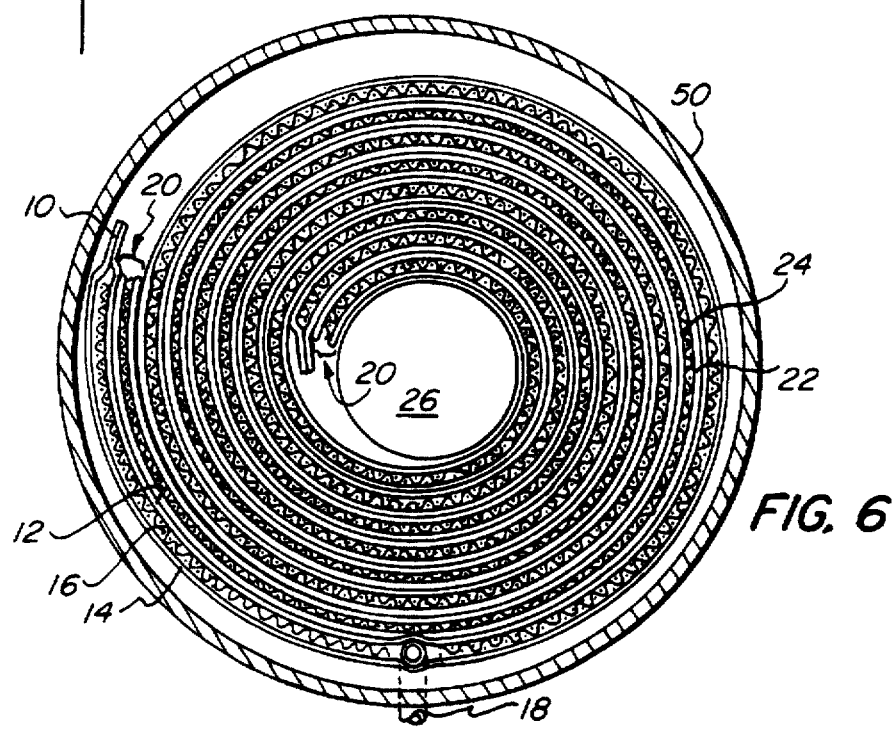
FIG. 6 is a sectional view, generally along 6—6 of FIG. 5, of an integral culture and gassing element of the invention.

The most Preferred embodiment of the invention in this respect is illustrated in FIG. 3. The cell substrate element 20 consists of a composite laminate of woven fiberglass sheets 22 (which, e.g., may be from about 100 to 300 microns in thickness) sandwiched about an inert spacer element 24 which may, for example, be a plastic material such as polypropylene. The substrate element is dimensioned so as to generally coincide with the length and transverse width dimensions of the membrane envelope 10, and is laid thereover before the winding operation. The layered arrangement of membrane envelope 10 and cell substrate element is then wound about itself, beginning with a first wind about supporting core element 26, to form an integral culture and gassing unit of predetermined length having a generally spiral or "jelly-roll" cross-section. As best seen in FIG. 6, the culture and gassing unit consists of spiral winds of membrane envelope 10 in which narrow annular cell culture spaces 30 are defined by the areas between adjacent winds. By reason of the lamination/winding process, these cell culture spaces contain a separate cell substrate element 20 on which cells can affix, or in association with which can be substantially immobilized, and grow.

When employed, supporting core element 26 has as its essential function the provision of longitudinal structural support to the membrane envelope and (where used) substrate material, and for this purpose can be formed of any suitable inert material, such as plastic, having a sufficient degree of rigidity. Particularly preferred are materials such as polycarbonates or fluorocarbon polymers such as polytetrafluoroethylene. For this purpose, the core element can be in the form of a solid rod- or cylinder- like element having a cross-sectional diameter appropriately large enough to provide support and to reduce circumferential differences between the two sides of the membrane envelope, but not so large as to result in the culture and gassing element itself having a cross-sectional diameter so large as to make its handling unwieldy. Alternatively, the core element 26 can be a hollow rod or cylinder capped at both ends to prevent flow of fluid therethrough. Still further, however, core element 26 can consist of a rigid hollow rod or cylinder whose walls are permeable (e.g. perforated) to permit flow therethrough. In this form, the inlet to the hollow core element can be connected, for example, to a gas source for passing therethrough of an oxygen-containing gas which can then flow through the wall perforations to provide additional oxygenation to the culturing cells in the cell culture spaces, particularly those in the culture space surrounding the core.

While the preferred embodiment of the invention, as shown in FIG. 3, utilizes a composite fiberglass cell substrate in the culture spaces, any number of alternative substrate materials and configurations also can be employed. The substrate material can, for example, comprise a compound or substance such as dextran, collagen, fibrin, polylysine or the like which is applied as a continuous or discontinuous layer to the outer facing surface of the top layer 12 of membrane envelope 10. Alternatively, as in the preferred embodiment, the substrate can be in the form of one or more sheets of any suitable inert material, such as cellulosic materials, woven fiberglass, woven ceramics, urethane foams, plastics and the like. These sheets similarly can be treated with compounds or substances which promote cell adhesion. The substrate can be in the form of a flat sheet, but also can be, for example, in a corrugated form to provide additional surface area for cell growth and, where desired, additional spacing between adjacent membrane envelope layers (i.e., enlarging of the cell culture spaces) to more easily accommodate flow of culture medium. As previously noted, the thickness of sheet-like substrates should be on the order of less than about 300 microns, and more preferably less than about 200 microns, owing to the fact that diffusional limitations are encountered in cell multilayers above about these thicknesses.

Figures 7, 8:
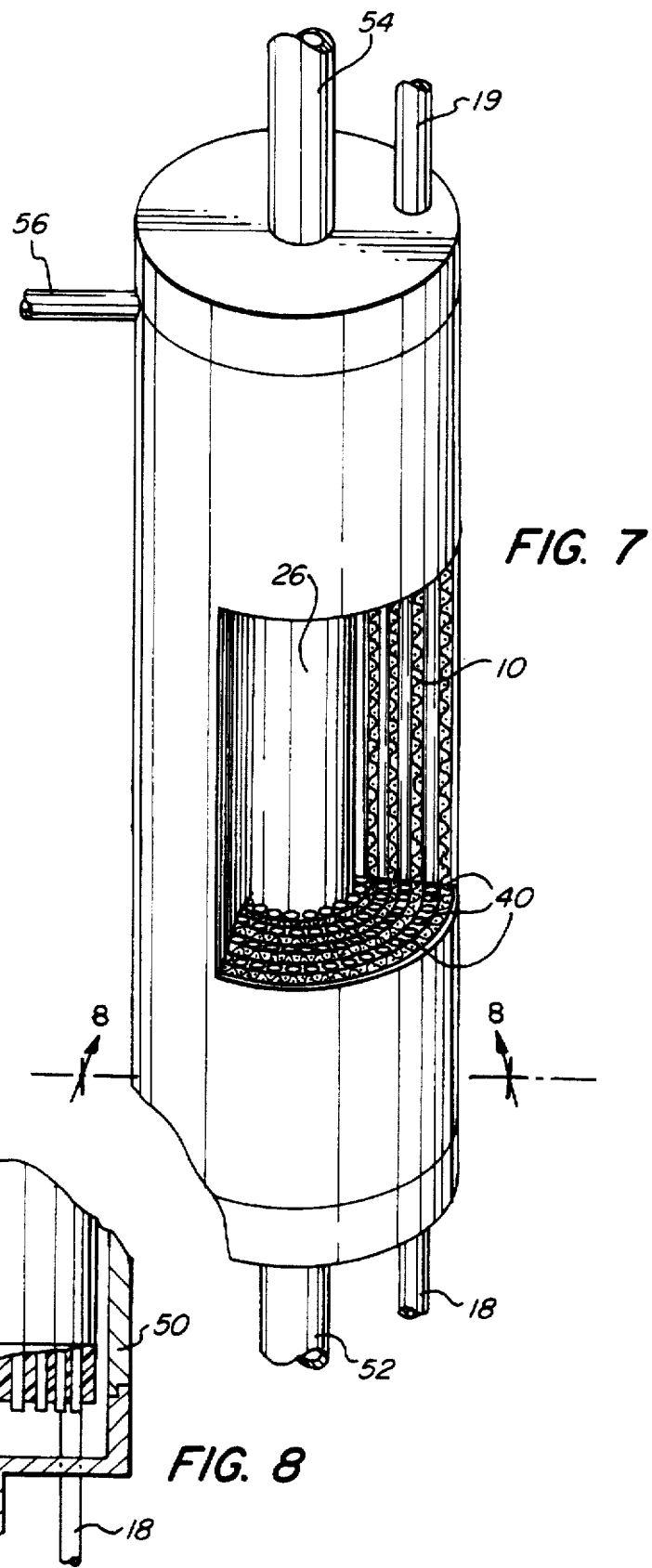
FIG. 7 is a longitudinal, partial sectional view of an alternative construction of a culture unit according to the invention.
FIG. 8 is a sectional view, along 8—8 of FIG. 7, demonstrating the utilization of hollow, semi-permeable fibers as substrates upon which cells grow and through which culture medium can be flowed and withdrawn.

One preferred alternative arrangement is shown in FIG. 7 wherein the substrate material is in the form of solid or hollow fibers (impermeable or semi-permeable) 40 formed of any suitable cell substrate materials and/or treated with compounds or substances promoting cell adhesion. In constructing the culture and gassing element according to this embodiment, a plurality of the fibers are arranged on the membrane envelope 10 transverse to the winding direction such that the winding operation results in fibers disposed in the cell culture spaces between adjacent winds of the membrane envelope and throughout the length of the culture spaces.

Within the context of this embodiment, a particularly preferred arrangement utilizes hollow, semi-permeable fibers as the cell substrate material arranged in the annular spaces between adjacent winds or lengths of the membrane envelope. In this embodiment, cells are cultured in these annular spaces in close association with the outer surfaces of the fibers in those spaces (or affixed thereto for adherent cells), and the fiber bores are utilized as the flow path for feed of nutrient medium and withdrawal of spent medium. As can be seen in FIG. 8, the hollow semi-permeable fibers 40 are chosen to be of a length which permits them to extend beyond the end faces of the membrane envelope 10. The extending ends of the plurality of hollow semi-permeable fibers can then be generally immobilized (i.e., potted) utilizing any appropriate material 60 (e.g., epoxy or other plastics) but leaving their ends open so that fluid can be fed into and withdrawn from the fiber bores. In operation then, nutrient medium is fed from one end of the integral culture and gassing unit so as to flow through the bores of the hollow semi-permeable fibers throughout their length. The permeability of the fibers is appropriately chosen to permit nutrients to permeate from the bore, across the fiber surfaces or walls, into the cell culturing areas (i.e., the annular spaces between adjacent winds or lengths of the membrane envelope), to there contact the cells. Waste products and any desired secreted cell products can be arranged to diffusionally flow from the culture spaces across the fiber walls and into the fiber bore for removal through the fibers at the opposite end face of the unit.

The foregoing embodiment is particularly preferred for non-adherent animal cells (e.g., hybridomas) which potentially could be swept out of the system if bathed in a nutrient medium flowing directly through the culture spaces. By arranging nutrient flow to be through hollow fibers, and then through the fiber walls into the culture spaces, immobilization and retention of the cells in the culture unit is greatly enhanced.

Preferably, where a cell substrate material is employed, it will be present in all the narrow annular culture spaces of the culture and gassing element and throughout the full length of each such space, as will be the case when the substrate is a sheet material layered over the membrane envelope and the culture and gassing element formed by a spiral winding or rolling operation. While preferred, however, it is not strictly necessary for the substrate element to be so arranged, and the present invention contemplates the presence of cell substrate material in less than all the cell culture spaces and/or along only a portion of the length of such spaces.

Figure 4:
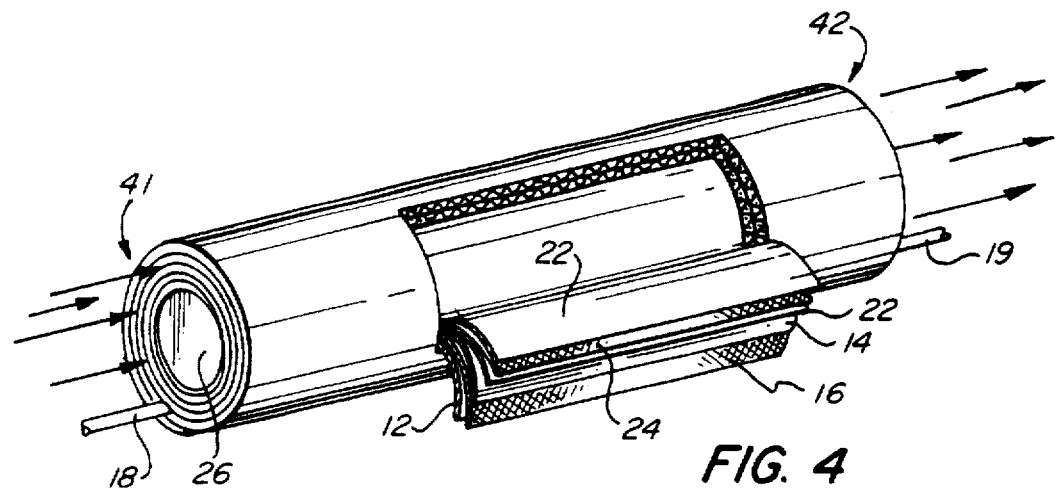
FIG. 4 is a perspective view of an assembled culture and gassing element according to the invention which has been diagrammatically sectioned to reveal internal components.
Figure 5:
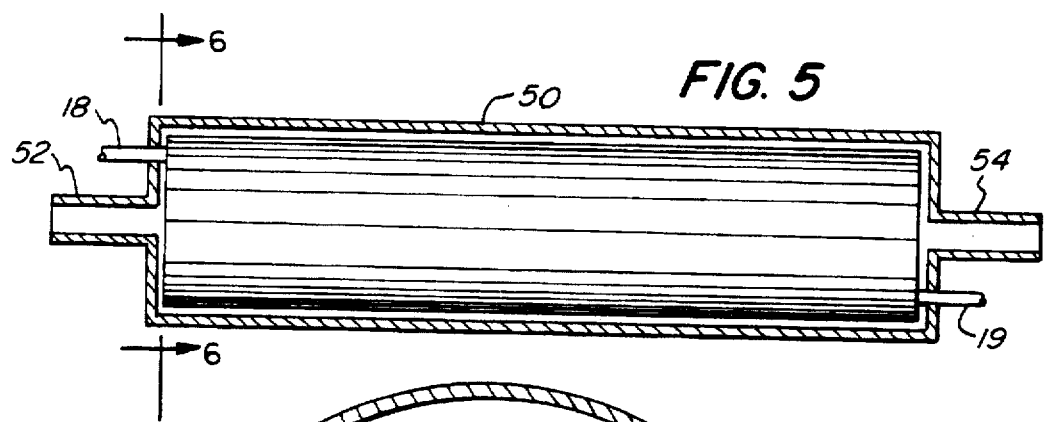
FIG. 5 is a longitudinal sectional view of a culture unit according to the invention in which the integral culture and gassing element is arranged in a fluid-tight housing.

As shown in FIG. 4 for the preferred embodiment of the invention, the culture and gassing element exhibits at each end thereof an inlet or outlet face (41, 42) through which culture medium can be introduced into the cell culture spaces and from which culture fluid can be removed from such spaces (e.g., directly or through hollow semi-permeable fibers). The element also will contain one or more sets of accessible gas inlet and gas outlet ports communicating with the interior of the membrane envelope 10. The element also can be provided with accessible ports communicating with the core element 26 in those embodiments where fluid (e.g., gas) is to be flowed through the core.

The so-constructed culture and gassing element is enclosed in any suitable fluid-tight housing 50 having liquid inlet and outlet ports (52, 54) and ports through which the gas inlet and gas outlet ports 18 and 19 of the membrane envelope may be accessed. The housing may also be provided with at least one port through which cells can be introduced into the culture and gassing element so as to occupy areas in the cell culture spaces, i.e., in the spaces between adjacent winds of the membrane envelope (whether provided with a separate cell substrate element or not). Alternatively, however, and except for the case where medium is flowed through hollow semi-permeable fibers, the cells can be introduced into the cell culture spaces by including them in initial charges of a culture medium flowed through the culture spaces.

For culturing cells in the apparatus of the invention, the culture unit (culture and gassing element enclosed within a fluid-tight chamber provided with suitable access parts) preferably is pre-sterilized and can then be arranged, either vertically or horizontally or in any other desired position on any suitable support member. Liquid inlet port 52 is connected by suitable sterile connections to a source of appropriate cell culture medium and the liquid outlet port 54 is similarly connected to an appropriate vessel or line through which culture fluid can be withdrawn, collected and processed. Gas inlet and gas outlet ports (18, 19) of the membrane envelope 10 are connected, respectively, to a source of oxygen-containing gas and to a line for drawing off gas. Where the membrane envelope is provided with a number of such gas inlets and/or outlets, these can be manifolded, within or outside the housing, into a single inlet or outlet line.

The culture unit is arranged in a suitable temperature-regulated environment, and cell stock inoculated into the culture and gassing element either through one or more inoculum ports (e.g., 56) generally arranged so as to be in proximity to the open inlet face of the spirally wound element, or by means of liquid flowed through the culture spaces. Culture medium is introduced into the culture unit liquid inlet port 52 and can, if desired, pass through a distributor means (e.g., a perforated plate) before contacting the inlet face of the spirally-wound culture and gassing unit so as to promote relatively even distribution of medium into the cell culture spaces defined by the adjacent winds of the membrane envelope. Where hollow semi-permeable fibers are employed, the introduction of culture medium through liquid inlet port 52 will result in the medium flowing through the open ends of the extending fibers and in that way eventually pass, at least in part, into the culture spaces. Initial flow and nutrient conditions are chosen to permit cells to become affixed to or associated with whatever substrate surface has been provided in the culture spaces, and thereafter can be optimized and controlled to effect desired flow rates and growth conditions. Culture fluid (i.e., spent culture medium together with any cell secreted products, wastes, etc.) is withdrawn from the opposite liquid outlet end 54 of the unit, either from the culture spaces per se or from the bores of hollow fibers arranged in those spaces.

During the culturing process, an oxygen-containing gas is supplied to the inlet ports of the membrane envelope and there diffuses across the gas-permeable layer or layers of the envelope into the surrounding adjacent cell culture spaces. Undiffused gas in the membrane envelope (and any gases transported across the membranes from cell space to envelope interior) exit the envelope through one or more gas outlet ports.

In the culturing process, the flows of inlet culture medium and inlet oxygen-containing gas may be continuous, pulsed, or intermittent. Preferably, culture medium can, at least periodically, be fed to the unit from the normally outlet end so as to promote, over the course of the culturing process, a relatively uniform nutrient environment in the culture spaces across the length of the unit irrespective of where along the length the cells reside. The housed culture unit can, if desired, be rotated about its core axis or subjected to any other gentle motion to promote a uniform culturing environment throughout the unit length and in all spaces between adjacent winds or lengths of the membrane envelope.

Culture fluid withdrawn from the culture unit can be processed in any number of ways depending upon desired aims. Thus, the fluid can be continuously or intermittently subjected to physical or immunochemical procedures for isolating therefrom any desired cell-secreted products, such as proteins, or can be treated to remove waste products therefrom so as to enable a recycling of some or all of the treated fluid to a make-up vessel for fresh culture medium, or other like procedures.

Ease of construction and permitting the culture spaces to be in fluid communication are primary reasons for the preferred embodiment of the invention constituting a culture and gassing unit in which the membrane envelope is spirally wound or rolled to assume a jelly-roll cross-section. Especially preferred is the formation of the culture and gassing element from a single given integral length of membrane envelope having an appropriate number of gas inlet and gas outlet ports. Alternatively, however, the element can be constructed from more than one such envelope, with a first being spirally wound for the number of winds possible, and a next envelope then being wound from the terminus of the last wind of the first envelope, and so on. In embodiments of this type, each such envelope will have its own independent gas inlet and gas outlet ports. All such ports can be manifolded so as to be in communication with a single gas inlet source and gas draw-off source or, alternatively, can be in communication with a separate, captive gas source and gas draw-off.

In alternative, although less preferred, constructions of the culture and gassing element, a plurality of lengths of membrane envelope can be used to form the element, each such length constituting a separate single wind over which the next length is wound or wrapped. In this manner, the culture and gassing element assumes a cylinder configuration in which there is present a series of generally concentric, generally annular lengths of separate membrane envelopes. The concentric, annular spaces between these concentric, annular lengths form cell culture spaces, but here the spaces are not in fluid communication, and each envelope length is required to have its own captive gas inlet and gas outlet ports for introduction and withdrawal of oxygen-containing gas into the interior of the envelope.

The culture and gassing element can be constructed so as to be of any suitable cross-sectional diameter and any suitable length from inlet face to outlet face. A number of the elements can be abutted in series throughout the length of a single fluid-tight housing.

The culture unit of the present invention can be utilized for the in vitro culturing of a variety of animal cells which produce and secrete products (e.g. proteins) of interest or whose mass growth is desired for other purposes. Particularly preferred are those cells which are capable of long-term growth and subdivision in culture, as is the case of various malignant cell lines and cells which have been immortalized by hybridization techniques. The invention also is applicable to the culture of animal cells which have been utilized as host cells in recombination techniques.

The invention is further illustrated with reference to the following examples.

EXAMPLE 1

An integral culture and gassing unit was constructed utilizing a liquid-impermeable, gas-permeable membrane envelope consisting of two lengths of gas-permeable dacron reinforced silicone rubber membrane (125 microns thick) sandwiched about a substantially equal length of polypropylene spacer, and the composite edge sealed. The assembled envelope had a transverse width of 26 cm and a length of 81 cm. A gassing port of silicone rubber was provided at one side of the envelope at one end of its length, and a second gassing port provided at the other end of its length and on the opposite side from that of the first port.

The membrane envelope was then provided with a cell substrate and spacer combination by layering onto one surface (i.e., one silicone rubber membrane surface) of the envelope, and substantially along its entire length and width, a first sheet of acid etched woven fiberglass cloth (150 microns thick), followed by an overlying 800 micron thick strand-on-strand polypropylene spacer (5.5 strands per cm), followed by an overlying sheet of the same woven fiberglass cloth used for the first layer.

The composite was then rolled about a solid core 4.5 cm in diameter and inserted into a polycarbonate sleeve having a diameter of 7 cm. End caps were installed on both ends of the sleeve, with each end cap bored centrally for introduction/withdrawal of fluid and also bored to permit exterior access to the gassing ports of the gassing and culture element. Thus, in the assembled configuration, cells attached to the glass fibers were presented with, on one side, an oxygen bearing surface and on the other side, a continually replenished source of medium flowing through the polypropylene mesh spacer.

The assembled unit was sterilized by autoclaving and placed in an incubator in which the temperature was maintained at 37° C. Approximately $1 \times 10^9$ Chinese hamster ovary (CHO) cells which secreted a heterologous protein resulting from genetic engineering were trypsinized, resuspended in basal medium supplemented with 5% fetal calf serum (FCS), and introduced uniformly into the cell culture device. The device was constructed so as to allow for a continual recirculation of culture medium through flexible tubing connected to either end of the device using peristaltic pumps. Twenty-four (24) hours after inoculation of the cells (a period sufficient to permit cell attachment within the culture unit), circulation of culture medium was initiated at a rate of 32 ml/min and continued at this rate for the duration of the culture period of 59 days. Using a timing device, the direction of flow of medium was regularly and periodically reversed throughout the culture period. Fresh medium supplement, in some cases containing 1% FCS, was added to the circulating liquid loop, while an equivalent volume of medium was withdrawn so as to maintain a constant medium volume in the culture chamber and to remove medium containing secreted proteins. Air supplemented with 5 to 15% carbon dioxide was directed through the gassing envelope at a rate of approximately 100 ml/min. Over the course of the 59 day culture period, process control was effected by changes in either gas composition or by increasing throughput of fresh medium so as to maintain predetermined critical pH and dissolved oxygen values at 6.9-7.1 and 80-120 mmHg, respectively. Using this apparatus and method, approximately 5-10 mg/day of the desired protein was produced.

EXAMPLE II

Approximately $4 \times 10^8$ fibroblast cells which were permissive host cells for a mammalian retro-virus and were chronically infected with that virus were trypsinized, suspended in basal medium supplemented with 5% fetal calf serum, and introduced uniformly into a cell culture chamber which was configured and operated identically to that described in Example I. Cells were maintained for a period of 97 days over which time 235 liters of conditioned medium were collected. Titers in the conditioned medium for one key viral antigen as measured by ELISA averaged approximately one-half to one-third those titers in conditioned media produced in roller bottle culture.

EXAMPLE III

Approximately $1-10^9$ human Bowes melanoma cells which constitutively secrete, among other proteins, tissue plasminogen activator (t-PA) were trypsinized, resuspended in basal medium supplemented with 5% fetal calf serum and introduced uniformly into a cell culture chamber in basal medium containing 5% fetal calf serum. The chamber, supporting apparatus, and operational procedures were essentially as described in Example I with the following exceptions.

The gas-permeable, liquid-impermeable membrane envelope was constructed of materials as described in Example I, but the longitudinal dimension was 243 cm while the lateral (transverse width) dimension was 26 cm. Two gas inlet and outlet ports were placed on each longitudinal edge and were offset from the opposed port by 80 cm. The lay-up schedule consisted of the edge-sealed envelope, 325 micron acid etched woven fiberglass cloth, and 800 micron strand-on-strand polypropylene spacer. The composite was rolled about a solid core 4.5 cm in diameter and inserted into a polycarbonate shell 9.5 cm in diameter. End caps were fitted and installed essentially as in Example I after gas ports on each end of the rolled composite were manifolded into a single inlet and outlet line operationally, the recirculation rate was varied between 280 and 504 milliliters per minute.

Cells were maintained within the cell chamber for 64 days. Over that period approximately 430 liters of conditioned basal media were collected which contained t-PA, as measured enzymatically using a fluorescent substrate, at a concentration up to twice that found in 24 hour conditioned media from confluent monolayers of cells conventionally grown in T-flasks.

EXAMPLE IV

Approximately $2-3 \times 10^8$ mouse hybridoma cells which secreted an $IgG_1$ monoclonal antibody were introduced into a cell chamber in basal medium supplemental with 5% fetal calf serum. This medium was also used subsequently. The cell chamber, supporting apparatus, and operational procedures were as described in Example I with the exception that medium flow throughout the recirculation loop and through the vertically oriented cell chamber was maintained in one direction only and in an upward direction.

After 23 days of operation, mouse immunoglobulin production, as measured by ELISA, was 230 mg/day, an amount consistent with the daily production from about $1 \times 10^{10}$ cells grown conventionally in basal medium supplemented with 10% fetal calf serum.

The foregoing description and examples are provided to assist in understanding of the invention, to describe the manner of its operation and to set forth the preferred methods, conditions and materials related thereto, but are not to be considered as limitations upon the scope of the invention as set forth in the appended claims.

What is claimed is:

1. A method for culturing animal cells comprising:
   (a) providing an integral culture and gassing element comprised of a plurality of generally concentric, generally annular lengths of an oxygen-permeable membrane envelope, said envelope comprised of an edge-sealed composite of a spacer layer sandwiched between a liquid impermeable base layer and a liquid-impermeable top layer, each of said base and top layers being permeable to oxygen, said oxygen-permeable membrane envelope having in communication therewith gas inlet means for providing an oxygen-containing gas to the enclosed spaces thereof and gas outlet means for removing gas from the enclosed spaces thereof, and wherein the area between adjacent lengths of said generally concentric annular lengths of said oxygen-permeable membrane envelope define narrow annular culturing spaces along said lengths for growth of animal cells in contact with culture medium, said culture and gassing element having a liquid inlet face at one end of the length thereof and a liquid outlet face at the opposite end of the length thereof by which culture liquid can be introduced to and withdrawn from said culturing spaces; said integral culture and gassing element being encased in a fluid-tight housing, said housing containing envelope access means for accessing said gas inlet and gas outlet means of said oxygen-permeable membrane envelope, liquid inlet means for introducing a flow of culture medium to the liquid inlet face of said culture and gassing element and liquid outlet means for removing culture liquid from said liquid outlet face of said culture and gassing element;

(b) providing in at least a portion of the length of at least some of the culturing spaces an inoculum of animal cells to be cultured;

(c) passing through said liquid inlet means of said housing a culture medium for said animal cells such that said culture medium passes through the length of at least some of the narrow annular culturing spaces and contacts cells contained therein;

(d) providing an oxygen-containing gas to said oxygen-permeable membrane envelope through said gas inlet means and withdrawing said gas through said gas outlet means, whereby, in passing from said gas inlet to said gas outlet means, at least a portion of said oxygen-containing gas diffuses across an oxygen-permeable layer of said envelope into the narrow annular culturing spaces; and (e) withdrawing culture fluid through said liquid outlet means of said housing.

2. The method according to claim 1 wherein the radially-innermost annular length of said oxygen-permeable membrane envelope surrounds a supporting inert core element of substantially the same length as said annular length.

3. The method according to claim 1 wherein at least a portion of at least some of said narrow annular culturing spaces contain a substrate material upon which animal cells can affix and/or become associated with and grow.

4. The method according to claim 3 wherein said substrate material is present throughout substantially all of said narrow annular culturing spaces.

5. The method according to claim 1 wherein said plurality of generally concentric, generally annular lengths of said oxygen-permeable membrane envelope consist at least in part of the spiral winds of a single oxygen-permeable membrane envelope, such that at least a portion of said narrow annular culturing spaces of said integral culture and gassing element are in fluid communication.

* * * * *